(12) United States Patent
Stark et al.

(10) Patent No.: US 11,221,396 B2
(45) Date of Patent: Jan. 11, 2022

(54) TRANSILLUMINATION OF THE SUBSURFACE, METHOD OF CAVITY DETECTION AND DETECTION CONFIGURATION

(71) Applicant: DIEHL DEFENCE GMBH & CO. KG, Ueberlingen (DE)

(72) Inventors: Robert Stark, Bad Windsheim (DE); Frank Sonnemann, Nurenberg (DE); Helmut Hofmann, Graefenberg (DE)

(73) Assignee: Diehl Defence GmbH & Co. KG, Ueberlingen (DE)

(*) Notice: Subject to any disclaimer, the term of this patent is extended or adjusted under 35 U.S.C. 154(b) by 386 days.

(21) Appl. No.: 16/442,746

(22) Filed: Jun. 17, 2019

(65) Prior Publication Data

US 2019/0383899 A1 Dec. 19, 2019

(30) Foreign Application Priority Data

Jun. 15, 2018 (DE) ...................... 10 2018 004 835.8

(51) Int. Cl.
*G01S 7/282* (2006.01)
*G01S 13/88* (2006.01)
(Continued)

(52) U.S. Cl.
CPC ............ *G01S 7/282* (2013.01); *G01S 13/885* (2013.01); *G01V 3/12* (2013.01); *A61B 5/0059* (2013.01);
(Continued)

(58) Field of Classification Search
CPC ...... A61C 9/0053; A61C 1/0088; G01V 3/12; G01S 7/282; G01S 13/885;
(Continued)

(56) References Cited

U.S. PATENT DOCUMENTS 3,020,471 A 2/1962 Barringer
3,831,173 A 8/1974 Lerner
(Continued)

FOREIGN PATENT DOCUMENTS

DE 4309599 A1 9/1994
DE 102009060657 A1 6/2011
(Continued)

*Primary Examiner* — Olumide Ajibade Akonai
(74) *Attorney, Agent, or Firm* — Laurence A. Greenberg; Werner H. Stemer; Ralph E. Locher (57) ABSTRACT

In a method for generating a transillumination signal of a section of the subsurface, an HPEM radiation source radiates an electromagnetic pulse into the section for the purpose of exciting electromagnetically reactive structures to emit an electromagnetic response signal. For the pulse, a pulse duration of at most 500 ns, a center frequency in the range between 10 MHz and 10 GHz, and a bandwidth in the range from 10% to 150% of the center frequency is set. The transillumination signal is formed as the sum of response signals received at a measuring location. In a method for detecting a cavity in the subsurface, the above method is carried out, and the structures are detected from the transillumination signal with the aid of a detection method, and the cavity is detected if the structures satisfy a detection criterion.

13 Claims, 4 Drawing Sheets

(51) Int. Cl.
*G01V 3/12* (2006.01)
*A61B 5/00* (2006.01)
*G01N 22/00* (2006.01)
*G01N 21/47* (2006.01)

(52) U.S. Cl.
CPC .......... *G01N 21/4795* (2013.01); *G01N 22/00* (2013.01)

(58) Field of Classification Search
CPC ...... G01S 13/0209; G01S 13/86; G01S 7/292; G01S 13/003; A61B 5/0059
See application file for complete search history.

(56) References Cited

U.S. PATENT DOCUMENTS

| | | | |
|---|---|---|---|
| 7,512,511 B1 * | 3/2009 | Schultz | F41H 13/0068 250/250 |
| 8,289,201 B2 * | 10/2012 | Holly | G01S 7/41 342/22 |
| 8,358,176 B2 | 1/2013 | Stark et al. | |
| 9,040,920 B1 * | 5/2015 | Hunt | G01V 3/12 250/340 |
| 9,851,440 B1 * | 12/2017 | Boyer | G01S 7/523 |
| 10,444,390 B2 * | 10/2019 | Van Der Doel | G01V 3/12 |
| 2009/0040093 A1 | 2/2009 | Holly et al. | |
| 2014/0125508 A1 * | 5/2014 | Stolarczyk | H01Q 1/521 342/22 |
| 2014/0125509 A1 * | 5/2014 | Stolarczyk | H01Q 1/521 342/22 |
| 2015/0153470 A1 * | 6/2015 | Stove | G01S 7/411 702/6 |
| 2018/0011212 A1 * | 1/2018 | Kang | G01V 3/12 |
| 2018/0045378 A1 * | 2/2018 | Kiliszewski | F21V 3/02 |

FOREIGN PATENT DOCUMENTS

| | | |
|---|---|---|
| EP | 1744177 A1 | 1/2007 |
| EP | 2144363 B1 | 5/2012 |

* cited by examiner

TRANSILLUMINATION OF THE SUBSURFACE, METHOD OF CAVITY DETECTION AND DETECTION CONFIGURATION

CROSS-REFERENCE TO RELATED APPLICATION

This application claims the priority, under 35 U.S.C. § 119, of German application DE 10 2018 004 835.8, filed Jun. 15, 2018; the prior application is herewith incorporated by reference in its entirety.

BACKGROUND OF THE INVENTION

Field of the Invention

The invention relates to a method for generating a transillumination signal of a section of the subsurface, to a method for detecting a cavity in the subsurface, to a detection arrangement having an HPEM radiation source and to the use of an HPEM radiation source.

The subsurface below the surface of the ground is naturally composed of a wide variety of materials, for example rock, sand, clay, water, crude oil/natural gas, ore deposits etc. In addition, the subsurface may contain naturally or artificially created cavities (caves, tunnels) or other artificially created or introduced materials (power/gas lines, railway tracks, submerged/buried articles etc.).

There is generally the desire to find out the nature of the subsurface from above the surface of the ground and, in particular, to detect and locate the above-mentioned materials and/or cavities. This has previously been possible substantially only by drilling operations, mining operations or by walking/driving on cavities.

The use of metal detectors or ground penetration radar (GPR) is known from practice. The penetration depth into the ground is limited in this case to a few metres or to the centimetre range. In particular, the process of finding irregularities in soil/rock layers by means of GPR or acoustic waves, metal and magnetic field sensors/detectors is known from practice. This also makes it possible to detect (concealed) tunnels or cavities to a limited extent.

SUMMARY OF THE INVENTION

The object of the invention is to propose improvements when examining the subsurface.

The object is achieved by means of a method for generating a transillumination signal of a section of the subsurface. Preferred or advantageous embodiments of the invention and of other invention categories emerge from the further claims, the following description and the accompanying figures.

In this case, the "section" is a volume, areal or linear region of the subsurface, in particular adjoining the surface of the ground. The areal region is, for example, a fan-like, layer-like or wafer-like region with a certain thickness which is small in comparison with the areal extent of the region. The linear region is, for example, rod-shaped, club-shaped or conical with a certain cross-sectional area which is small in comparison with the longitudinal extent of the region.

In the method, a high-power-electro-magnetics (HPEM) radiation source radiates at least one electromagnetic pulse into the section. The pulse is used to excite possible electromagnetically reactive structures present in the section. As a result of the pulse impinging on such a structure, the latter is excited to emit an electromagnetic response signal. Such structures are, for example, electrically conductive devices such as power lines (in particular in a tunnel or cavities, for example for illumination purposes) or embedded metallically conductive ores in the rock (which surrounds, in particular, a tunnel or a cavity). The structures are excited to themselves emit electromagnetic fields by fast electromagnetic HPEM pulses in the picosecond or nanosecond range by exciting electrical currents and voltage pulses. These electromagnetic fields form the response signal.

A pulse duration of at most 500 ns and a centre frequency in the range between 10 MHz and 10 GHz are selected for the pulse. In addition, a bandwidth which is selected in the range of 10% to 150% of the center frequency is selected for the pulse.

In the method, the transillumination signal is formed as the sum of possible response signals received at a measuring location.

The frequency content of the pulse is determined by the pulse shape. A typical pulse has a rise time of 1 ns, for example, for a pulse duration of 5 ns to 7 ns. A pulse which is accordingly short according to the invention results in an expansion of the frequency content. A broadband system (many frequencies, for example 20% to 100% of the centre frequency, for example a bandwidth of 150 MHz for a center frequency of 300 MHz) is used according to the invention. This differs, for example, from a radar system which operates, for instance, in the region of a frequency of 1 MHz.

In other words, the response signal constitutes an echo signal to the pulse which is generally emitted at least in different directions, in particular in a spherical manner from the echo source (electromagnetically reactive structure). At least one part of the response signal is received at a measuring location selected in a defined manner when the response signal has sufficient (measurable) signal strength.

A pulse duration of at most 100 ns, at most 50 ns, at most 10 ns, at most 5 ns or at most 3 ns is selected, in particular, for the pulse. The center frequency is selected, in particular, in the range between 100 MHz and 5 GHz, between 250 MHz and 3 GHz or between 500 MHz and 2 GHz. The bandwidth is selected, in particular, between 15% and 125%, between 20% and 100%, between 30% and 90% or between 40% and 80% of the center frequency.

In one preferred embodiment, a rise time of at most 5 ns, at most 4 ns, at most 3 ns, at most 2 ns, at most 1 ns or in the picosecond range is selected for the pulse. In this case, the rise time should be understood in the manner conventional in practice, that is to say between 10%/90% thresholds or 20%/80% thresholds, for example.

If the section or part of the section irradiated by the pulse does not contain an electromagnetically reactive structure, a zero signal results as the transillumination signal. If, although there is a corresponding structure, the pulse at the location of the structure is too weak to perform any noticeable excitation or the response signal at least at the measuring location is below a measurability limit, no portion in the transillumination signal arises for this structure.

The section is, in particular, that region of the subsurface to which the pulse is "applied". This should be understood as meaning the fact that the section comprises only that region of the subsurface in which the pulse still has sufficient energy to actually be able to excite structures possibly present there to reflection which can still be measured at the measuring location.

Any conventional suitable fast metrology which is able to detect corresponding reflected or emitted pulses (response signals) can be used to receive the response signals at the measuring location.

As a result, the method provides the transillumination signal which can then be subsequently evaluated in any desired manner. For example, conclusions with regard to the depth (distance from the radiation source and/or the measuring location) of the presumed structure can be obtained from the propagation time behaviour and/or the pulse length/shape (for example rise time) and/or the frequency/amplitude distribution of the response signals reflected/emitted by the structure. Presumed tunnels/cavities and their spatial course can also be inferred using detected structures.

Powerful electromagnetic pulses from HPEM sources/pulse sources are used for the method. Considerably greater ranges and penetration depths or detection depths of up to several tens of metres or deeper can be achieved as a result of the high signal amplitude (several kV/m to several MV/m) and the spectral range used (several MHz to several GHz). The spectral range used also allows good spatial and time resolution. The pulse amplitude, signal profile (rise time, pulse duration, frequency content) and ground conditions decisively determine the possible sensitivity and spatial resolution of the system. For example, the sensitivity of the detector technology, the number of detectors and the corresponding evaluation algorithm play a decisive role.

In one preferred embodiment of the invention, an initial field strength in the range between 10 kV/m and 10 MV/m is selected for the pulse during its emission. In particular, the initial field strength is selected between 100 kV/m and 5 MV/m, between 250 kV/m and 3 MV/m or between 500 kV/m and 2 MV/m. In this case, the "initial field strength" is the field strength of the pulse immediately after leaving the radiation source or upon entering the section. The corresponding field strength ensures sufficient ranges for irradiating the subsurface and sufficient potential for exciting electromagnetically reactive structures.

In one preferred embodiment, a total electromagnetic power in the range between 10 MW and 10 GW is selected for the pulse. In particular, the total power is selected in the range between 100 MW and 5 GW, between 250 MW and 3 GW or between 500 MW and 2 GW. The corresponding power likewise ensures sufficient ranges for irradiating the subsurface and sufficient potential for exciting electromagnetically reactive structures.

In one preferred embodiment of the method, the pulse is generated with the aid of an electrical voltage inside the radiation source. In this case, the voltage has a signal amplitude in the range of 10 kV to 10 MV. In particular, the voltage has a signal amplitude in the range of 100 kV to 5 MV, 250 kV to 3 MV or 500 kV to 2 MV. The above-mentioned pulses can be generated in a particularly effective manner, in particular, by corresponding voltages.

In one preferred embodiment of the method, the pulse is generated with the aid of an electrical voltage inside the radiation source having a (temporal) DS (damped sinusoid) profile. The result is also a corresponding temporal profile of the electromagnetic radiation in the pulse. Corresponding pulses are suitable, in particular, for generating meaningful response signals. An high-power-electro-magnetics/damped sinusoid (HPEM-DS) radiation source is known, for example, from European patent EP 2 144 363 B1.

In one preferred embodiment, the pulse is generated as the sum pulse of at least two individual pulses from temporally synchronized individual sources. In this case, all of the individual sources form the HPEM radiation source. The statements made above with respect to the radiation source analogously apply to the individual sources. It is possible to increase the power further in the method as a result of the plurality of parallel individual sources. A single pulse source or antenna for emitting the pulse therefore suffices in the method. However, a plurality of antennas (temporally synchronized, for temporally synchronized individual or partial pulses) can also be used, in particular. These partial pulses are then added to form the actual (sum) pulse.

In one preferred embodiment, the pulse is radiated into the section from above (air space, atmosphere, surface of the ground) the subsurface. Radiation sources can be fitted in a particularly simple manner there.

In one preferred embodiment, the measuring location is selected above the subsurface. Measuring apparatuses can be fitted in a particularly simple manner there.

The object is also achieved by means of a method for detecting a cavity in the subsurface. In the method, the above-mentioned method according to the invention for generating the transillumination signal is carried out. Possible electromagnetically reactive structures are then detected in the section from the transillumination signal with the aid of a detection method. A cavity is detected in the section when the detected structures satisfy a detection criterion.

Any desired detection methods, for example conventional signal processing and assessment for classifying response signals, are conceivable here. Any desired detection criteria are also conceivable. Merely by way of example, a corresponding detection criterion is, for example, the checking of a threshold value. If the signal strength of the transillumination or response signals correlated with the structures is below the threshold value, only less reactive structures than expected are present in the section. The section must therefore contain a region without structures. This indicates a cavity. A detection criterion could also be the fact that a structure in the form of railway tracks or supply lines is detected, which indicate the presence of a corresponding tunnel in which the railway tracks or supply lines are installed. Any desired detection criteria are conceivable here depending on the application.

In one preferred embodiment of the method, a relative position of the detected structures in the section is determined from the transillumination signal with the aid of a localization method. The cavity is then determined in those regions of the section which satisfy a localization criterion of the localization method. In particular, the position of the cavity in the subsurface is then determined from the known relative position of the section in the subsurface and the relative position of the cavity in the section.

Any desired localization methods, for example conventional reconstruction or tomography methods, are conceivable here. Any desired localization criteria are also conceivable. The localization criterion is, in particular, the fact that a cavity is present at those locations of the section at which no structures are detected. The relative position of the section in the subsurface is known, for example, from the location and/or the direction of the emission of the pulse, the radiation location/direction of the pulse into the section, the position of the measuring location, the beam direction of the response signals, etc.

The proposed method therefore makes it possible to detect, for example, electrically conductive devices such as lines in the tunnel/cavity, from which it is possible to infer the course of the tunnel/cavity. In contrast to other methods, tunnels and cavities deep in the ground/in the rock can also be detected.

The invention therefore results in a method for finding concealed tunnels and/or cavities using HPEM. The examined region (section) is irradiated with a powerful pulsed/modulated (CW—continuous wave, pulsed) HPEM source. Electrically conductive cables, articles, ores in the tunnel/cavity or in the surrounding wall are excited to emit radiation. The tunnel/cavity can be detected and optionally also located by analysing (time, frequency, etc.) the reflected pulses (transillumination signal). According to the invention, tunnels are therefore located and detected, in particular.

The cavity can also be located by "scanning" a larger region of the subsurface with successive, "small" sections. For each section, a cavity is then detected or is not detected (in a binary manner) for the section. The positionally accurate concatenation of the sections or the detection results then forms an overall image of the region from parts of cavity sections and solid sections.

In one preferred embodiment, respective transillumination signals are formed at at least two different measuring locations. The structure is detected from at least two of the transillumination signals with the aid of a combining detection method (and detection criterion) (combining the transillumination signals and their mutual relationship) and/or—if present—the position of the cavity in the subsurface is determined with the aid of a combining localization method (and localization criterion). The quality, in particular spatial resolution, of the method can be effected or improved during detection/localization by a plurality of measuring locations.

The object of the invention is also achieved by means of a detection arrangement. The arrangement contains an HPEM radiation source which is set up to generate a pulse for the method according to the invention for generating the transillumination signal. The detection arrangement also contains a receiver for receiving the response signals according to the relevant method. In particular, the detection arrangement contains the above-mentioned voltage source for generating the electrical voltage for the pulses. In particular, the detection arrangement contains at least two temporally synchronized individual sources, as described above, and a relevant synchronization unit. In particular, the detection arrangement contains a plurality of receivers which can be placed at different measuring locations.

The detection arrangement and at least some of its embodiments and the respective advantages have already been analogously explained in connection with the methods according to the invention.

In one preferred embodiment, the detection arrangement contains a control and evaluation unit which is set up to carry out the method according to the invention for detecting a cavity in the subsurface.

This embodiment of the detection arrangement and at least some of its embodiments and the respective advantages have also already been analogously explained in connection with the methods according to the invention.

The object of the invention is also achieved by a use of an HPEM radiation source to carry out the method according to the invention for generating a transillumination signal and by use of an HPEM radiation source to carry out the method according to the invention for detecting a cavity in the subsurface.

The uses and at least some of their embodiments and the respective advantages have already been analogously explained in connection with the methods according to the invention and the detection arrangement according to the invention.

The invention is based on the following knowledge, observations and considerations and also has the following embodiments. In this case, the embodiments are partly also called "the invention" in a simplifying manner. In this case, the embodiments may also contain parts or combinations of the embodiments mentioned above or may correspond thereto and/or may possibly also include embodiments which have not been previously mentioned.

The invention deals, in particular, with a method for detecting hidden tunnels and spaces using HPEM. The method/measuring method and an apparatus for carrying out the latter consist of an HPEM high-power EM source/pulse source and corresponding fast detection method/probes. The emitted powerful electromagnetic pulse excites electrically conductive cables, articles, connections or else ore deposits (electromagnetically reactive structures) present in the environment of the tunnel to themselves emit radiation via the injected pulses. The rise time of the pulses is typically in the ps to ns range with pulse widths of a few ps to several 100 ns and pulse amplitudes around several kV/m to several MV/m. The emitted frequency range may extend over a wide range (typical frequencies: a few 10 MHz to several GHz).

As a result of the induced voltages and currents, a characteristic spectrum (response signal) is again emitted (by the structures), which spectrum is decisively determined by the arrangement and the course of lines, metallically conductive articles or conductive ore deposits. Information relating to the arrangement and the course of the metallic components is obtained by comparing the received signals (transillumination signal) with the emitted signals (pulse), thus again indicating hidden tunnels and cavities.

The measuring method is a completely new approach to detecting tunnel systems or concealed cavities. The use of pulsed HPEM high-power sources enables detection at much greater depths than previously possible in comparison with established methods. The temporal synchronization of a plurality of electromagnetic HPEM radiation sources (individual sources) with one another and with the associated measuring diagnostics (including a plurality of sensors/sensor technologies at a plurality of measuring locations) makes it possible to further increase the sensitivity and the detection probability of the system/method.

If there are metal ores and loosely connected metal conductive components in the rock, a further effect can additionally be used with this technology. As a result of the very short rise times and short pulse lengths of the HPEM pulses, displacement currents and "transfer discharges" are excited at the transition points/discontinuities and a characteristic spectrum is emitted, the spectrum providing information relating to the distribution of the metallizations/presence of metal/ore-containing deposits and their spatial distribution. These metallizations are absent in the tunnel or cavity itself, with the result that characteristic differences arise here in the reflected frequency behavior, the attenuation behavior and in the time behavior/delay of the pulses, from which the presence and the course of a tunnel or a cavity can be extracted.

The use of pulsed HPEM high-power sources enables detection at much greater depths than previously possible in comparison with the established methods. The temporal synchronization or deliberate desynchronization of a plurality of electromagnetic radiation sources or HPEM pulses (individual sources/pulses) with one another and with the measuring diagnostics (including a plurality of sensors/sensor technologies/measuring locations) makes it possible to further increase the sensitivity, the detection probability and the spatial resolution of the system.

Other features which are considered as characteristic for the invention are set forth in the appended claims.

Although the invention is illustrated and described herein as embodied in a transillumination of the subsurface and cavity detection, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
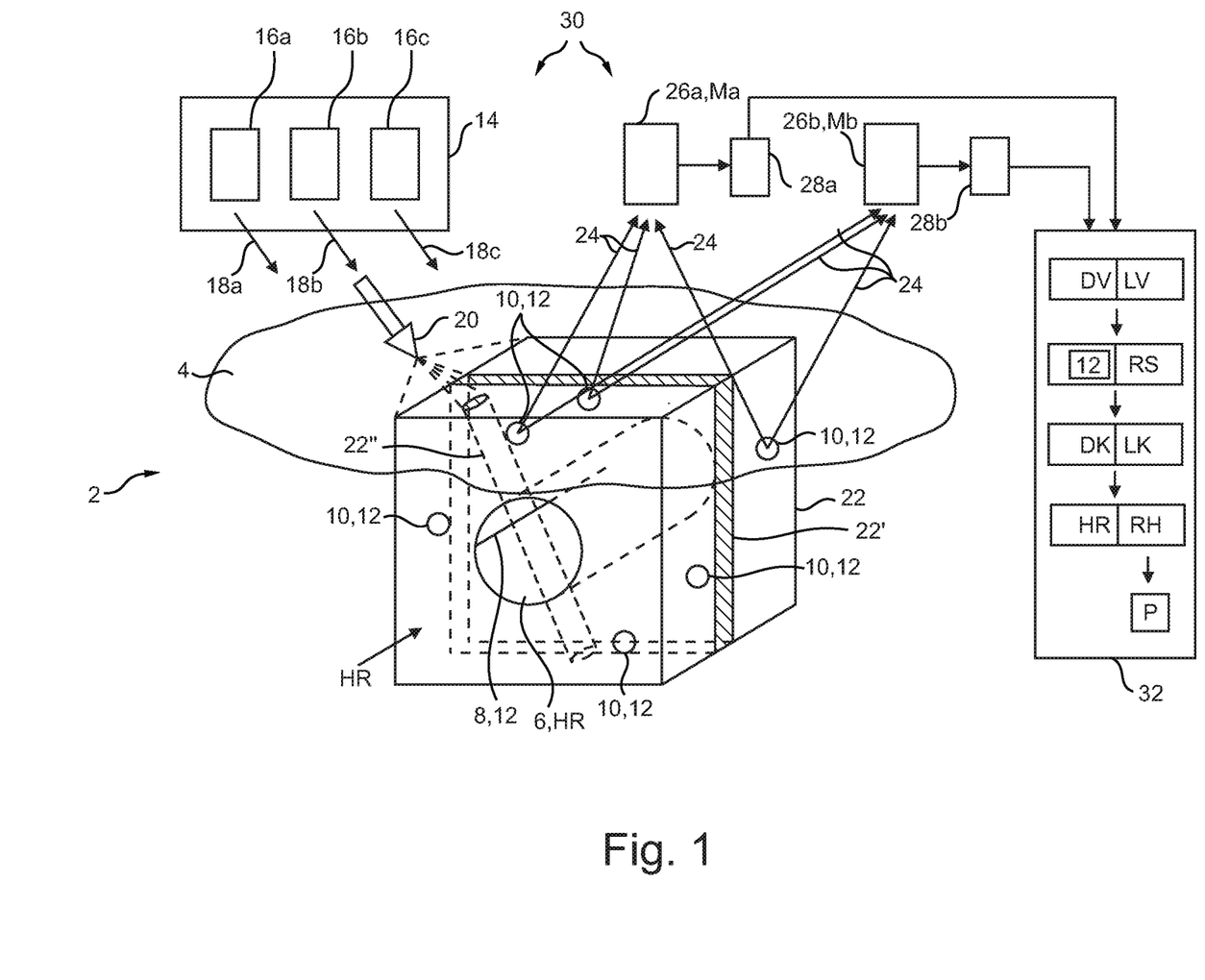
FIG. 1 is an illustration of a section of ground with a tunnel and a detection arrangement during operation.

Referring now to the figures of the drawings in detail and first, particularly to FIG. 1 thereof, there is shown a section of ground or subsurface 2 below the surface of the ground 4. A concealed tunnel 6 runs in the subsurface 2. An electrical supply line 8 for illuminating the tunnel is laid in the tunnel 6. Electrically conductive ore deposits 10 which are indicated only symbolically here are also contained in the subsurface 2. Both the supply line 8 and the ore deposits 10 are electromagnetically reactive structures 12.

An HPEM radiation source 14 is situated above the surface of the ground 4. The source 14 contains a plurality of individual sources, three individual sources 16a to 16c in the example. Each of the individual sources 16a to 16c is set up to emit an electromagnetic individual pulse 18a to 18c. The individual sources 16a to 16c and therefore the individual pulses 18a to 18c are temporally synchronized with one another, with the result that the individual pulses 18a to 18c are added to form a single electromagnetic pulse 20 in the form of a sum pulse of the individual pulses 18a to 18c. The pulses are each symbolized by arrows. In the example, the pulse 20 is not an omni-directional pulse, but rather is directed in a particular main direction but is spatially extended in this case, with the result that it overall applies considerable electromagnetic radiation to a volume section 22 of the subsurface 2. This is indicated by dashed lines. For the sake of simplicity, the section 22 is symbolized as a cube in the figure. In alternative applications, the pulse 20 has a fan-like form, with the result that it applies radiation only to a planar section 22', or is linear, with the result that it applies radiation only to a linear section 22"; such alternative sections 22', 22" are indicated in FIG. 1.

The pulse 20 has a rise time of 1 ns (from 10% to 90% of the maximum amplitude), a pulse duration of 5 ns, a center frequency of 300 MHz and a bandwidth of 150 MHz. A generating voltage in the radiation source 14 for the pulse 20 has a DS temporal profile and amplitude of 1 MV. The field strength of the pulse 20 upon entering the surface of the ground 4 is 1 MV/m and its total energy content is 1 GW.

The structures 12 are therefore referred to as electromagnetically reactive since they themselves are excited to reflect or emit a respective electromagnetic response signal 24 or act accordingly as a result of the radiation or impingement of the pulse 20. In this case, depending on the type of structure 12, the response signal 24 is emitted by the respective structures 12 in an undirected (for example spherical) manner or in a directed manner (in a particular direction).

Two receivers 26a, 26b for receiving the respective response signals 24 are arranged at two different measuring locations Ma, Mb above the surface of the ground 4, wherein only that respective portion of the response signal 24 which also arrives there is received in the respective receiver 26a, 26b. Corresponding response signals 24 or parts of the latter are therefore likewise symbolized in FIG. 1 by arrows towards the receiver 26a, 26b and are indicated only for some of the structures 12. In each of the receivers 26a, 26b, the response signals 24 respectively arriving there are added to form a respective transillumination signal 28a, 28b. The radiation source 14, together with the receivers 26a, 26b, is part of a detection arrangement 30.

The detection arrangement 30 also contains a control and evaluation unit 32 which is set up to carry out the now described method.

The detection arrangement first of all causes the generation of the transillumination signals 28a, 28b of the section 22 of the subsurface 2 in the following manner: the radiation source 14 emits the electromagnetic pulse 20. In this case, the pulse 20 is generated as a sum pulse of the individual pulses 18a to 18c. The pulse 20 excites the electromagnetically reactive structures 12 present in the section 22 to emit respective electromagnetic response signals 24. This takes place specifically as a result of the pulse 20 impinging on the structures 12. The transillumination signal 28a, 28b is formed as the sum of the response signals 24 respectively arriving at one of the receivers 26a, 26b.

Inside the control and evaluation unit 32, structures 12 are then detected in the section 22 from the two transillumination signals 28a, 28b with the aid of a combining detection method DV (combined evaluation of both transillumination signals 28a, 28b). The detected structures 12 are now checked with the aid of a detection criterion DK. In the example, the transillumination signals 28a, 28b correlated with the structures 12 are compared here with a threshold value. Since the latter is not exceeded, it is concluded that the entire section 22 is not occupied by reactive structures 12. The section 22 must therefore also contain a cavity HR, here in the form of the tunnel 6.

The following method is also carried out in the control and evaluation unit 32: a relative position RS of the structures 12 in the section 22 is determined with the aid of an accordingly combining (see above) localization method LV. The cavity HR is then determined in those regions of the section which satisfy a localization criterion LK. In the example, these are all regions of the section 22 in which no structures 12 were determined on the basis of their relative positions RS. The corresponding regions therefore also have a relative position RH of the cavity HR in the section 22. The position P of the cavity HR in the subsurface 2 is determined from the relative position RH and from the known relative position of the section 22 in the subsurface 2 or with respect to the detection arrangement 30.

Figure 2:
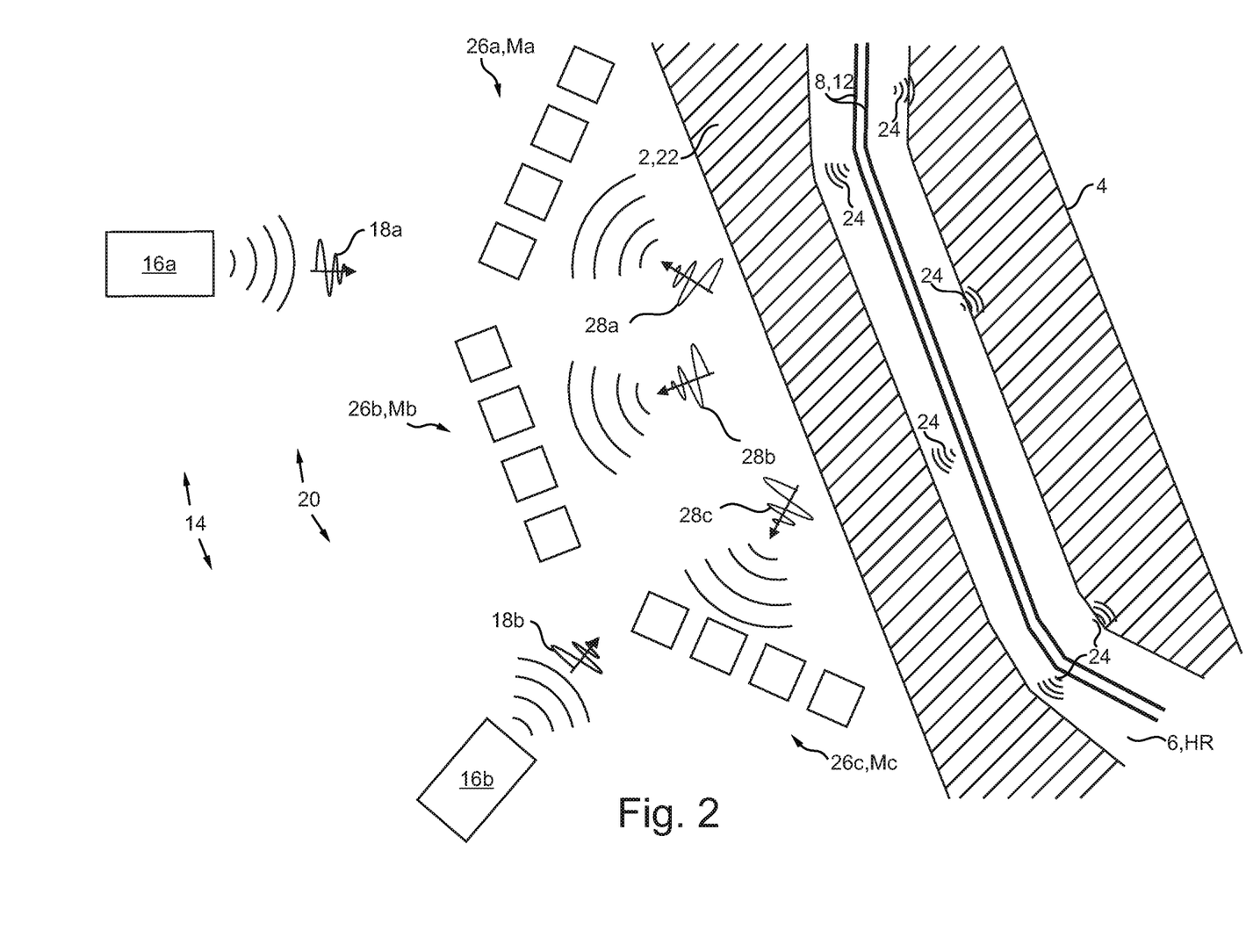
FIG. 2 is an illustration showing an alternative section of the ground with the tunnel and lines and the detection arrangement.

FIG. 2 shows an alternative section 22 of the subsurface 2 (soil, wall, rock material), likewise again with a tunnel 6 in which two electrical lines in the form of supply lines 8 are laid. In this case, the radiation source 14 contains two spatially distributed individual sources 16a, 16b which emit individual pulses 18a, 18b in a temporally synchronized manner, which individual pulses are again added to form a common pulse 20 (not specifically illustrated).

Figure 3:
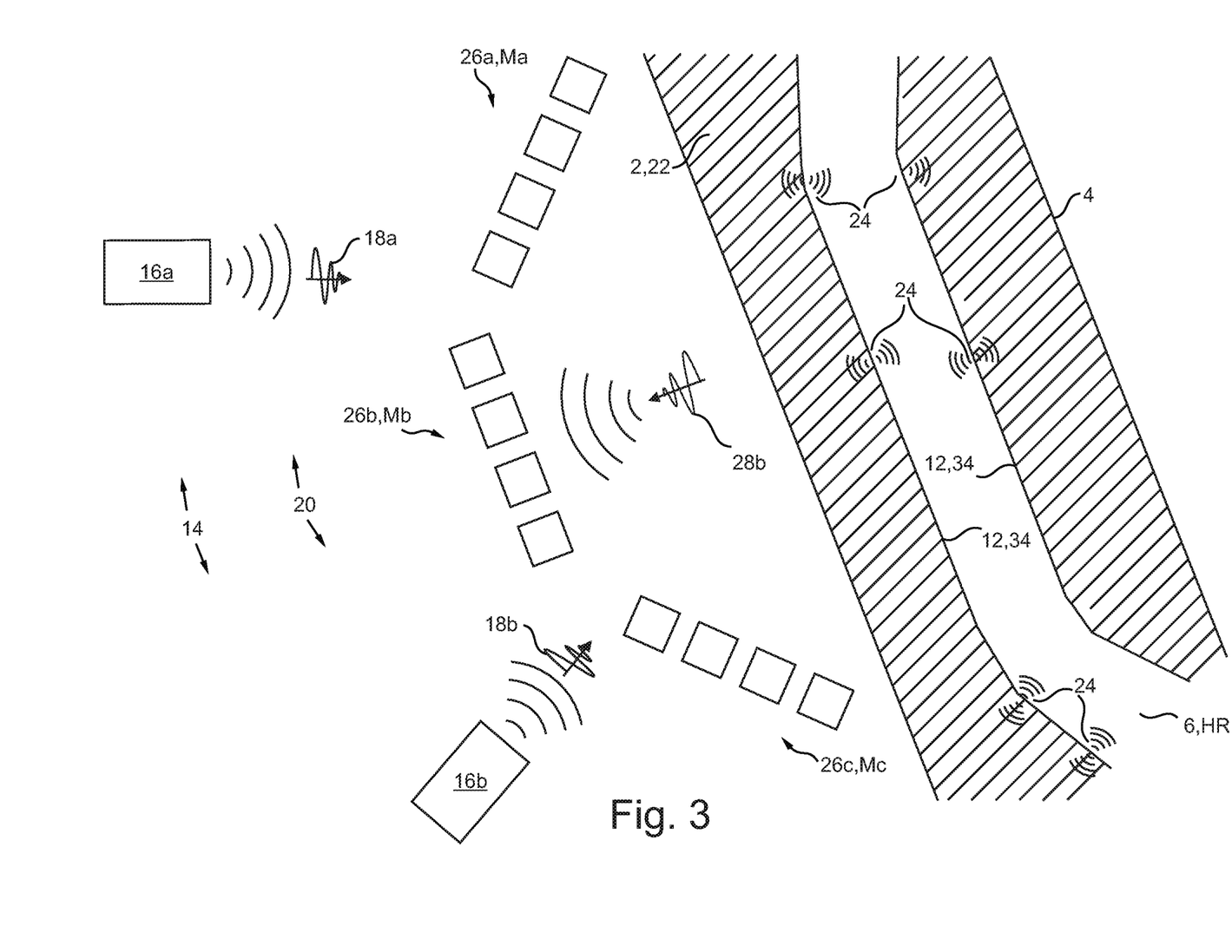
FIG. 3 is an illustration showing the section from FIG. 2 without lines.
Figure 4:
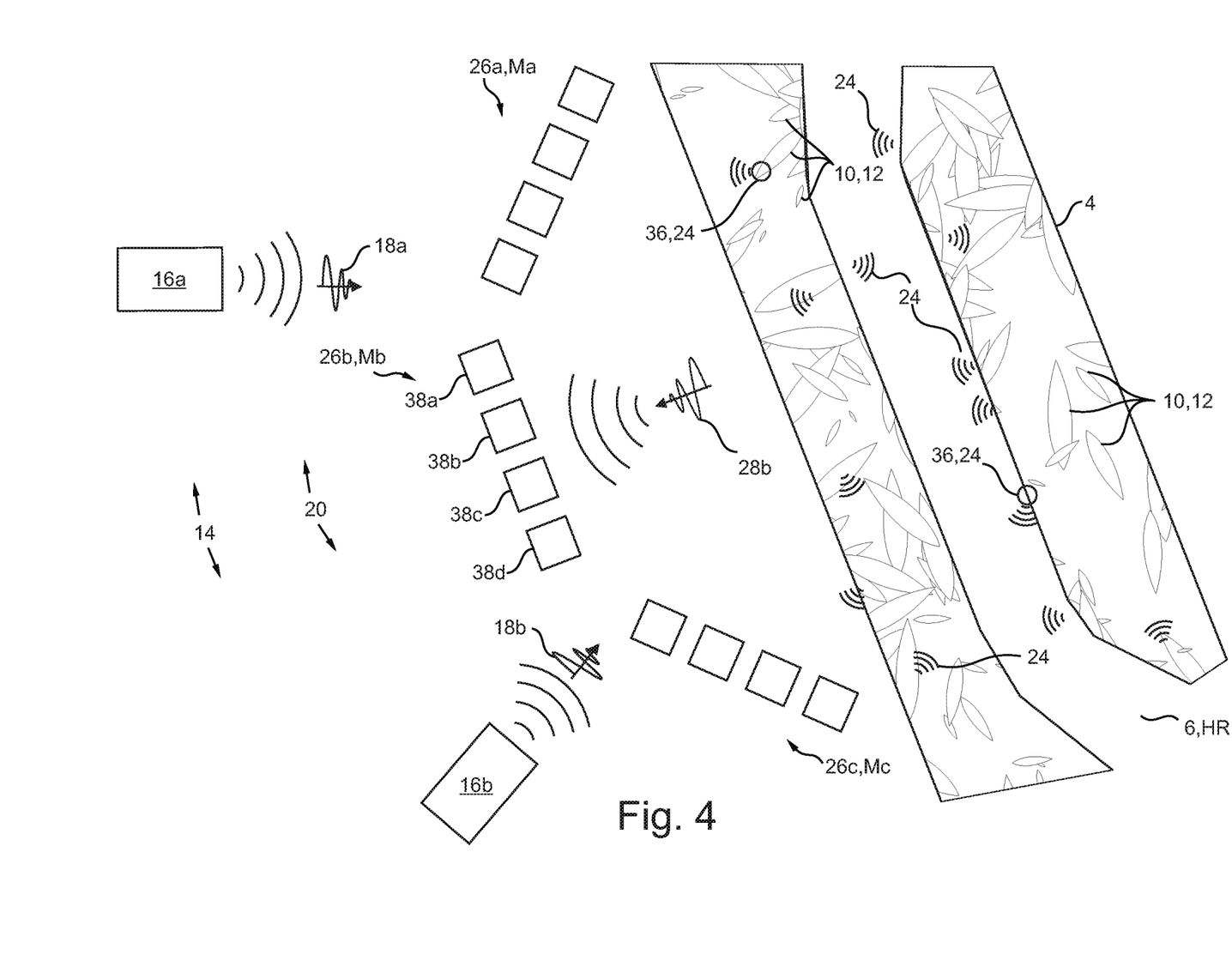
FIG. 4 is an illustration showing the section from FIG. 2 with ore deposits surrounding the tunnel.

In this case, a total of three receivers 26a to 26c are provided at measuring locations Ma to Mc and receive and forward three transillumination signals 28a to 28c (only the signal 28b is shown, by way of example, in FIGS. 3 and 4). Each of the receivers 26a to 26c is in the form of a quadruple sensor array here. According to this embodiment, each of the receivers 26a to 26c is therefore formed by an RF sensor 38a, an IR sensor 38b, a sensor 38c for visible light and a UV light sensor 38d.

According to FIGS. 2 to 4, one or, here, more powerful (kW to GW) radio-frequency HPEM radiation sources (individual sources 16a, 16b) emit one or more electromagnetic pulses 20 (one illustrated here) which penetrate the soil or the rock (subsurface 2). If the electromagnetic pulse 20 strikes a metallically conductive wire—only the supply nine 8 is shown in isolation in FIG. 2—or ores etc. (see below), corresponding voltages and currents are induced in said wire. The induced currents/displacement currents in turn emit electromagnetic waves as response signals 24, which waves also emit a characteristic frequency spectrum depending on the length and nature of the electrically conductive wires (also deposits/cables/articles, see below). In FIG. 2, this is illustrated for the emission of the response signals 24 (here EM emission) by the supply line 8.

FIG. 3 shows the situation from FIG. 2, in which case the supply lines 8 have been omitted here for the sake of clarity. In comparison with FIG. 2, FIG. 3 illustrates the following: in addition (to the reflection by the lines 8 as a response signal 24, see above), sudden impedance changes occur in the material at the tunnel walls 34 as EM reactive structures 12, which sudden impedance changes can be additionally used to detect the tunnel. This is also symbolically illustrated by the emission of response signals 24 at the tunnel walls 34.

With a sufficiently high electrical field strength and a sensitive measuring system/sensors (receivers 26a to 26c), long ranges and detection even at relatively great depths are possible. The sensitivity of the measuring method can be improved further by using a plurality of HPEM-DS sources (individual sources 16a, 16b) and sensors (receivers 26a to 26c) which can be temporally matched to one another (synchronized, desynchronized).

FIG. 4 also again shows the situation from FIG. 3, in which case the supply lines 8 have likewise been omitted here and the electrically conductive ore deposits 10 in the form of metallically conductive ores in the subsurface 2 are symbolically illustrated. These also form EM reactive structures 12. If, as illustrated in FIG. 4, the surrounding material of the tunnel 6 consists of metallically conductive ores, the powerful HPEM pulses 20 generate electrical currents in the vein of ore or the metal deposits and the individual filaments and generate electrical potential differences in adjacent metallizations. With a sufficiently high electrical field strength, transfer discharges or transient discharges, for example surface discharges, spark discharges or point discharges, can be observed at the ends of the filaments or at the transition points between the filaments, joints and discontinuities. The discharge currents/current distributions which are formed generate a broad electromagnetic frequency spectrum (response signal 24) which can be detected as relatively broadband "characteristic noise", for example in the radio-frequency range or another spectral range (IR to UV; in the case of deposits close to the surface, here represented by two discharge flashes 36, indicated by a circle).

The response signals 24 from FIGS. 2 to 4 are superimposed to form the transillumination signals 28a to 28c. The tunnel 6 or cavity HR is then detected and located as described above with respect to FIG. 1.

The following is a summary list of reference numerals and the corresponding structure used in the above description of the invention:

2 Subsurface
4 Surface of the ground
6 Tunnel
8 Supply line
10 Ore deposit
12 Structure
14 Radiation source
16a to 16c Individual source
18a to 18c Individual pulse
20 Pulse
22 Section
24 Response signal
26a to 26c Receiver
28a to 28c Transillumination signal
30 Detection arrangement
32 Control and evaluation unit
34 Tunnel wall
36 Discharge flash
38a to 38d Sensor
Ma to Mc Measuring location
DV Detection method
DK Detection criterion
HR Cavity
LV Localization method
LK Localization criterion
RS Relative position (structure)
RH Relative position (cavity)
P Position

The invention claimed is:

1. A method for generating a transillumination signal for a section of a subsurface, which comprises the steps of:
providing a high-power-electro-magnetics radiation source radiating at least one electromagnetic pulse into the section for exciting electromagnetically reactive structures present in the section resulting in an emission of an electromagnetic response signal when the electromagnetic pulse impinges;
setting a pulse duration of the electromagnetic pulse to be at most 500 ns;
forming the electromagnetic pulse to have a center frequency in a range between 10 MHz and 10 GHz;
forming the electromagnetic pulse to have a bandwidth in a range from 10% to 150% of the center frequency; and
forming the transillumination signal as a sum of response signals received at a measuring location.

2. The method according to claim 1, which further comprises setting an initial field strength in a range between 10 kV/m and 10 MV/m for the electromagnetic pulse during its emission.

3. The method according to claim 1, which further comprises selecting a total electromagnetic power in a range between 10 MW and 10 GW for the electromagnetic pulse.

4. The method according to claim 1, which further comprises generating the electromagnetic pulse with an aid of an electrical voltage from the HPEM radiation source having a signal amplitude in a range of 10 kV to 10 MV.

5. The method according to claim 1, which further comprises generating the electromagnetic pulse with an aid of an electrical voltage from the HPEM radiation source having a damped sinusoid profile.

6. The method according to claim 1, which further comprises generating the electromagnetic pulse as a sum pulse of at least two individual pulses from temporally synchronized individual sources as the HPEM radiation source.

7. The method according to claim 1, which further comprises radiating the electromagnetic pulse into the section from above the subsurface.

8. The method according to claim 1, which further comprises selecting the measuring location from above the subsurface.

9. A method for detecting a cavity in a subsurface, which comprises the steps of:
  generating a transillumination signal by providing a high-power-electro-magnetics radiation source radiating at least one electromagnetic pulse into a section of the subsurface for exciting electromagnetically reactive structures present in the section resulting in an emission of an electromagnetic response signal when the electromagnetic pulse impinges;
  setting a pulse duration of the electromagnetic pulse to be at most 500 ns;
  forming the electromagnetic pulse to have a center frequency in a range between 10 MHz and 10 GHz;
  forming the electromagnetic pulse to have a bandwidth in a range from 10% to 150% of the center frequency;
  forming the transillumination signal as a sum of response signals received at a measuring location;
  detecting the electromagnetically reactive structures in the section from the transillumination signal with an aid of a detection method; and
  detecting a cavity in the section if the electromagnetically reactive structures detected satisfy a detection criterion.

10. The method according to claim 9, which further comprises:
  determining a relative position of the electromagnetically reactive structures detected in the section from the transillumination signal with an aid of a localization method; and
  determining the cavity in regions of the section which satisfy a localization criterion of the localization method.

11. The method according to claim 9, which further comprises:
  forming respective transillumination signals at at least two different measuring locations, and a electromagnetically reactive structure is detected from at least two of the transillumination signals with an aid of a combining detection method; and/or
  determining a position of the cavity in the subsurface with the aid of a combining localization method.

12. A detection configuration, comprising:
  an high-power-electro-magnetics radiation source for generating a transillumination signal by radiating at least one electromagnetic pulse into a section for exciting electromagnetically reactive structures present in the section resulting in an emission of an electromagnetic response signal when the electromagnetic pulse impinges, a pulse duration of the electromagnetic pulse being set to be at most 500 ns, the electromagnetic pulse having a center frequency in a range between 10 MHz and 10 GHz, the electromagnetic pulse having a bandwidth in a range from 10% to 150% of the center frequency and the transillumination signal formed from a sum of electromagnetic response signals received at a measuring location; and
  a receiver for receiving receivable parts of the electromagnetic response signals.

13. The detection configuration according to claim 12, further comprising a control and evaluation unit set up to:
  detect the electromagnetically reactive structures in the section from the transillumination signal with an aid of a detection method; and
  detect a cavity in the section if the electromagnetically reactive structures detected satisfy a detection criterion.

* * * * *